United States Patent [19]

Gijzen et al.

[11] Patent Number: 5,438,613
[45] Date of Patent: Aug. 1, 1995

[54] X-RAY ANALYSIS APPARATUS AND SCANNING UNIT SUITABLE FOR USE IN SUCH AN APPARATUS

[75] Inventors: Wilhelmus A. H. Gijzen; Walterus A. L. A. Van Egeraat; Johannes P. M. Van Alen, all of Almelo; Albert Visscher, Eindhoven, all of Netherlands

[73] Assignee: U.S. Philips Corporation, New York, N.Y.

[21] Appl. No.: 993,342

[22] Filed: Dec. 18, 1992

[30] Foreign Application Priority Data

Dec. 18, 1991 [EP]   European Pat. Off. .......... 91203343

[51] Int. Cl.[6] .............................................. G01T 1/36
[52] U.S. Cl. .......................................... 378/82; 378/83
[58] Field of Search ........................... 378/82, 83, 84

[56] References Cited

U.S. PATENT DOCUMENTS 3,123,710  3/1964  Neuhaus .......................... 250/51.5
4,637,041  1/1987  Brinkgreve et al. .................. 378/84

*Primary Examiner*—Craig E. Church
*Attorney, Agent, or Firm*—Jack D. Slobod

[57] ABSTRACT

An X-ray analysis apparatus includes a scanning unit (1) with an X-ray source (3), a crystal holder (9) and an X-ray detection system (5) provided with an X-ray detector (7). The crystal holer (9) can be rectilinearly displaced in a fixed radiation pick-up direction (35) relative to the X-ray source (3). The crystal holder (9) and the X-ray detector (7) are mechanically coupled to one another via a plate (21) which can be driven by means of a motion mechanism. The X-ray source (3), the X-ray detector (7) and the crystal holder (9) remain positioned on a Rowland circle (11) during the displacement. The motion mechanism has a first guide (23) and a second guide (25). The drive direction of the first guide (23) encloses an acute angle α relative to the fixed pick-up direction (35).

20 Claims, 8 Drawing Sheets

X-RAY ANALYSIS APPARATUS AND SCANNING UNIT SUITABLE FOR USE IN SUCH AN APPARATUS

BACKGROUND OF THE INVENTION

1. Field of the Invention

The invention relates to an X-ray analysis apparatus, comprising a scanning unit with an X-ray source, a crystal holder which can be rectlinearly displaced in a fixed radiation pick-up direction relative to the X-ray source, an X-ray detection system with an X-ray detector and a motion mechanism for effecting a coupled displacement of the crystal holder and the X-ray detector, the X-ray source, the crystal holder and the X-ray detector remaining on a Rowland circle during said displacement. The invention also relates to a scanning unit suitable for use in an X-ray analysis apparatus such as a simultaneous spectrometer or a sequential spectrometer.

2. Description of the Related Art

A Rowland circle is to be understood to mean herein a focusing circle of a diameter corresponding to the radius of curvature of an analysis crystal situated on said circle, an X-ray source and a detector entrance also being situated on said circle. The choice of the radius R of the Rowland circle is very important in view of the resolution of the apparatus.

An X-ray source is to be understood to mean herein a point on the Rowland circle on which the radiation to be analysed is focused. This point may be situated on a specimen to be analysed, for example in the case where a comparatively small region of the specimen is locally excited by means of an X-ray beam or an electron beam. On the other hand, this point may also coincide with a centre of a slit wherebehind a specimen to be analysed is arranged for excitation. Furthermore, the region to be analysed can be localized by means of a slit on the X-ray detector.

An X-ray analysis apparatus of the kind set forth is known from U.S. Pat. No. 3,123,710. An X-ray analysis apparatus described therein utilizes a scanning unit with a focusing optical system in which, during the measurement process, the crystal is rectlinearly displaced along a fixed line, referred to as the pick-up direction, relative to a fixed point, notably the X-ray source. The detector is at the same time displaced along a path whose origin coincides with the fixed point. In order to sustain the focusing conditions between the X-ray source, the crystal and the detector during the motion, these three components are situated on a focusing circle, i.e. the Rowland circle. In order to ensure that the crystal is rectilinearly displaced in a fixed direction, the Rowland circle should be tilted about the X-ray source during the motion. The choice of the X-ray source as the fixed point is justified by the fact that the specimen to be analysed is thus always analysed with the same pick-up conditions.

This motion is realised by positioning the analysis crystal between the X-ray source and the detector on the Rowland circle, the surface of the analysis crystal being coincident with the Rowland circle. The analysis crystal and the detector are then mechanically interconnected, for example via an anchor-like element as in the cited United States Patent Specification. This element can be driven by means of a linear motion mechanism. In the cited Patent Specification this motion mechanism consists of a worm-wheel-worm drive and a guide.

A drawback thereof consists in the comparatively poor reproducibility and the occurrence of play. Such a drive can be rendered play-free by applying a bias. The reproducibility is closely related to inter alia the magnitude of said bias and the rigidity of the system.

SUMMARY OF THE INVENTION

It is an object of the invention to provide an X-ray analysis apparatus of the kind set forth which achieves at least the same precision whereas the mechanical requirements to be satisfied by the scanning unit are substantially less severe.

To achieve this, the X-ray analysis apparatus in accordance with the invention is characterized inter alia in that the motion mechanism of the scanning unit comprises a first guide which can be displaced along a line, referred to as the drive direction, from a drive point, and a second guide which can be displaced along a line, referred to as the shift direction, from a shift point, the drive direction of the first guide enclosing an acute angle of relative to said fixed pick-up direction. Because the drive direction of the guide encloses an angle $\alpha$ relative to the direction of motion of the crystal, the distance over which the guide is to be displaced so as to realise an angular variation $\Delta\theta$ is greater than the corresponding distance travelled by the crystal. Consequently, a possibly non-reproducible adjustment of the guide will have a substantially smaller effect than when the crystal is driven in the direction of motion, so that less severe mechanical requirements need be satisfied. The costs are thus also reduced. Moreover, more space is available for the crystal holder.

A special embodiment of the X-ray analysis apparatus in accordance with the invention is characterized in that the second guide is constructed as an elastic guide, the shift point being coincident with a point on the Rowland circle which is displaced by only a comparatively small amount when the crystal holder is displaced between successive positions. Because of the position of the bearing point of this guide, also referred to as the shift point, the displacement thereof for the various crystal positions is sufficiently small, so that the use of an elastic guide suffices. This position of minimum displacement is determined by the choice of the angle $\gamma$, being the angle enclosed by the drive direction with respect to the shift direction. An advantage of an elastic guide consists in that there is no play, so that the reproducibility of guiding is substantially better than that of a normal guide. Moreover, an elastic guide is substantially less expensive.

A further embodiment of the X-ray analysis apparatus in accordance with the invention is characterized in that the crystal holder and the X-ray detector are mechanically coupled to one another via a Rowland plate which can be driven by the motion mechanism and which comprises points of attachment for the crystal holder, for the first guide, for the second guide and for a drive centre wherefrom the X-ray detector can be driven. In this manner, the crystal holder itself is not manipulated, resulting in more freedom as regards the design of the crystal holder.

A further embodiment of the X-ray analysis apparatus in accordance with the invention is characterized in that adjacent the points of attachment the amount of material of the Rowland plate is minimized while sustaining adequate rigidity. When the volume of the Rowland plate is thus limited, it becomes more compact and hence more readily movable. Moreover, more structural space is created for other parts of the scanning unit, if any.

An embodiment of the X-ray analysis apparatus in accordance with the invention is characterized in that the drive centre is coincident with the centre of the Rowland circle. Despite the comparatively complex detector motion, the detector is then driven from a fixed point, being a comparatively simple operation.

A further embodiment of the X-ray analysis apparatus in accordance with the invention is characterized in that at the centre of the Rowland circle a segment of circle is secured so as to be pivotable, the detector being mechanically coupled to said segment of circle and a rolling wire, biased by a tension wire, being guided on said segment of circle which can roll along said rolling wire in order to impart to the detector a pivot motion linked to the motion of the crystal holder.

Due to the coupled motion of the crystal holder and the detector, the centre of the Rowland circle performs a circular motion about the X-ray source. The detector motion will also satisfy the requirements imposed, i.e. movement along the Rowland circle, when the detector is driven from this centre with the suitable transmission ratio relative to a fixed reference point.

A further embodiment of the X-ray analysis apparatus in accordance with the invention is characterized in that the radius of the segment of circle amounts to 1/6 of the diameter of the Rowland circle. The desired transmission ratio can be achieved by way of a suitable choice of the radius of the segment of circle.

A further embodiment of the X-ray analysis apparatus in accordance with the invention is characterized in that at the drive centre there is provided a first drive wheel whereto the detector is mechanically coupled, at the shift point there being provided a second drive wheel, a drive belt being guided on said drive wheels and the ratio of the diameters of the drive wheels being defined by the desired transmission ratio. Regardless of whether or not the drive centre for the detector motion coincides with the centre of the Rowland circle, this is a suitable possibility for achieving coupled motion of the crystal and the detector. The desired transmission ratio is again achieved by a suitable choice of the diameters of the drive wheels.

A further embodiment of the X-ray analysis apparatus in accordance with the invention is characterized in that on the Rowland plate there is secured an arm having a length substantially equal to $$\tfrac{1}{2} 2R/\cos\Delta,$$

its points of attachment being the shift point of the second guide and the drive centre whose position is determined by the length of the arm and a direction which encloses a fixed angle $\psi$ relative to the shift direction, the X-ray detector being mechanically coupled to said arm via the drive centre, 2R being the diameter of the Rowland circle and $\Delta$ being a deviation of $\theta$ relative to $\gamma + \alpha$, being an angle enclosed by the shift direction and the fixed pick-up direction. The resolution to be achieved in the X-ray analysis apparatus is determined to a great extent by the distance between the analysis crystal and the X-ray source. The distance should have a minimum value so as to minimize the effect of irregularities in the crystal and to enable reproducible measurements. Notably for heavier elements, i.e. for smaller angles, the source-crystal distances are comparatively small. The minimum distance value required can be obtained by increasing the Rowland circle which, however, may give rise to comparatively large dimensions of the Rowland plate. The Rowland plate, and hence also the X-ray analysis apparatus, can remain compact when the drive centre does not coincide with the centre of the Rowland circle.

A further embodiment of the X-ray analysis apparatus in accordance with the invention is characterized in that for directional adjustment the detector is mounted on a mounting bracket on which there is provided a runner which can run on a track provided adjacent the detector. In order to orient the detector towards the crystal, correction of the viewing direction is desirable; this is achieved by means of the described step. The path described also suppresses detector motions in the direction perpendicular to the plane of motion, resulting in a substantial improvement of the rigidity of the system in the direction perpendicular to the plane of motion.

An alternative embodiment of the X-ray analsysis apparatus in accordance with the invention in which a correction of the viewing direction is achieved is characterized in that for directional adjustment of the detector a guide roller is secured to the crystal holder, a wire which is tensioned between on the one side the X-ray detector and on the other side a fixed point situated outside the Rowland circle and in a virtual prolongation of the fixed pick-up direction being guided on said guide roller.

An embodiment of the X-ray analysis apparatus in accordance with the invention is characterized in that the first guide is driven by means of a step motor.

An alternative embodiment of the X-ray analysis apparatus in accordance with the invention is characterized in that the first guide is driven by means of a servo positioning system. The choice between these two alternatives for the drive system for the first guide is governed by the requirements imposed on the guide as well as by the costs. The guide should be drivable in small steps. A step motor offers high-quality guiding in view of the requirements imposed as regards hysteresis and linearity, and hence its cost price is high. A servo positioning system imposes less severe requirements on the guide, because it is used in combination with a measuring ruler. The position of the guide can then be optically sensed and electronically recorded. The quality of guiding is then determined by the optical sensing and not by the mechanics, so that the mechanical requirements are substantially less severe.

A further embodiment of the X-ray analysis apparatus in accordance with the invention is characterized in that the crystal holder of the scanning unit is constructed as a crystal turret. The diameter of the Rowland circle determines the feasible $\theta$ range for the scanning unit. The feasible range of elements is determined by the choice of the crystal. In order to enable detection of elements in a comparatively large range of elements, therefore, measurement using more than one diffraction crystal is desirable. When a crystal turret is used, crystals can be exchanged comparatively quickly.

Range of elements is to be understood to mean herein the group of elements having an atomic number between that of borium and uranium.

A further embodiment of the X-ray analysis apparatus in accordance with the invention is characterized in that the crystal turret can be driven in two directions.

When both directions of rotation are used for scanning, the analysis crystal can be exchanged faster.

A further embodiment of the X-ray analysis apparatus in accordance with the invention is characterized in that the crystal holder comprises a control device for the crystal position. Diffraction crystals generally exhibit a given degree of asymmetry. The lattice faces do not extend strictly parallel to the crystal surface. Using a crystal position control device, correction can be made so that the spread in the position of the focus on the detector can be minimized. Moreover, correction for small mechanical tolerances is thus also possible.

A further embodiment of the X-ray analysis apparatus in accordance with the invention is characterized in that the detector comprises a detection slit which forms part of a beam limiter. The signal-to-background ratio improved by compensation for a limited space angle.

An embodiment of the X-ray analysis apparatus in accordance with the invention, conceived as a simultaneous spectrometer comprising a number of fixed channels, is characterized in that at least one of the fixed channels is replaced by a scanning unit. By replacing a fixed channel in an X-ray analysis apparatus conceived as a simultaneous spectrometer by a scanning unit in accordance with the invention, such a spectrometer will have the speed of a simultaneous spectrometer and the flexibility of a sequential spectrometer. The higher sensitivity on the one hand and the possibility of simultaneous measurement on the other hand will result in a substantial reduction of the measurement time per specimen. The use of more than one scanning unit means an increase of the throughput of specimens, and hence a reduction of the costs per measurement.

An alternative embodiment of the X-ray analysis apparatus in accordance with the invention, conceived as a sequential spectrometer having a scanning range, is characterized in that the scanning range is a scanning sub-range to be scanned by the scanning unit. The radius of the Rowland circle is closely related to the feasible range of elements for the apparatus. The intended range of elements (B-U) requires tilting of the Rowland circle through an angle of 66°. Requirements in respect of selectivity and background radiation impose restrictions as regards the distance to be chosen between the X-ray source and the crystal. For heavier elements the source-crystal distances are comparatively large, implying comparatively large focusing circles for smaller angles. This results in bulky constructions when larger angles are also to be adjusted. When the scanning unit is made suitable for a limited range of elements, and hence a limited range of angles, the radius of the Rowland circle is determined per sub-range and hence per scanning unit. Consequently, the apparatus can be more readily adapted to specific requirements of a customer, so that the price-performance ratio can be substantially improved. Moreover, more than one X-ray detector is required anyway to enable scanning of the range of elements B-U, so that it can be specifically chosen for a scanning sub-range without additional steps being required.

BRIEF DESCRIPTION OF THE DRAWING

The invention will be described in detail hereinafter with reference to the drawing. Corresponding pans are denoted by corresponding reference numerals in the various Figures, wherein.

DETAILED DESCRIPTION OF THE PREFERRED EMBODIMENT

Figure 1:
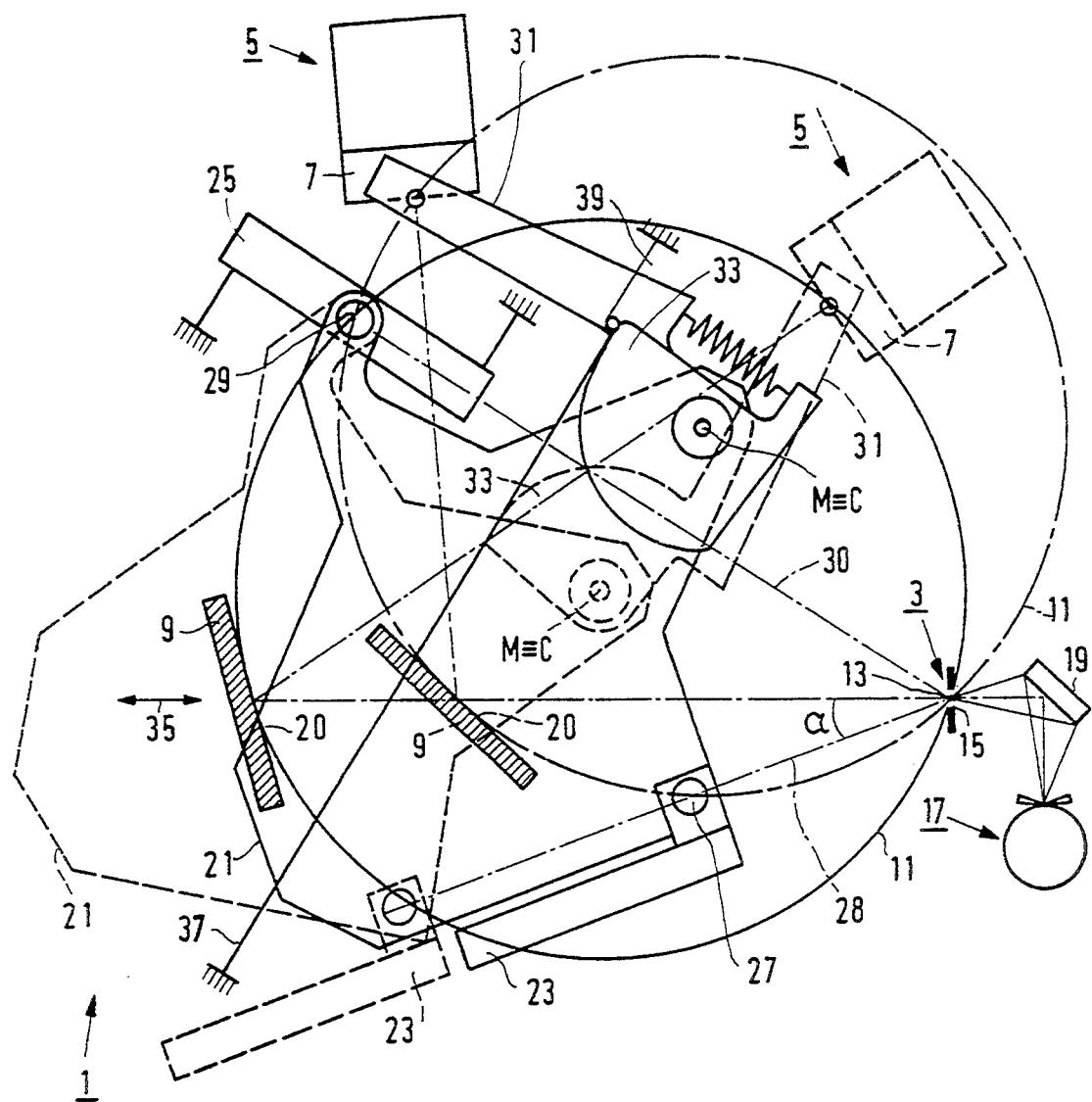
FIG. 1 shows diagrammatically a first embodiment of a scanning unit for an X-ray analysis apparatus in accordance with the invention in which the detector is driven from the centre of the Rowland circle.

The scanning unit 1 for an X-ray analysis apparatus as diagrammatically shown in FIG. 1 in accordance with the invention comprises an X-ray source 3 and an X-ray detection system 5 with an X-ray detector 7. The scanning unit 1 also comprises a crystal holder 9 which is represented by a single analysis crystal for the sake of simplicity of FIG. 1.

Figure 2:
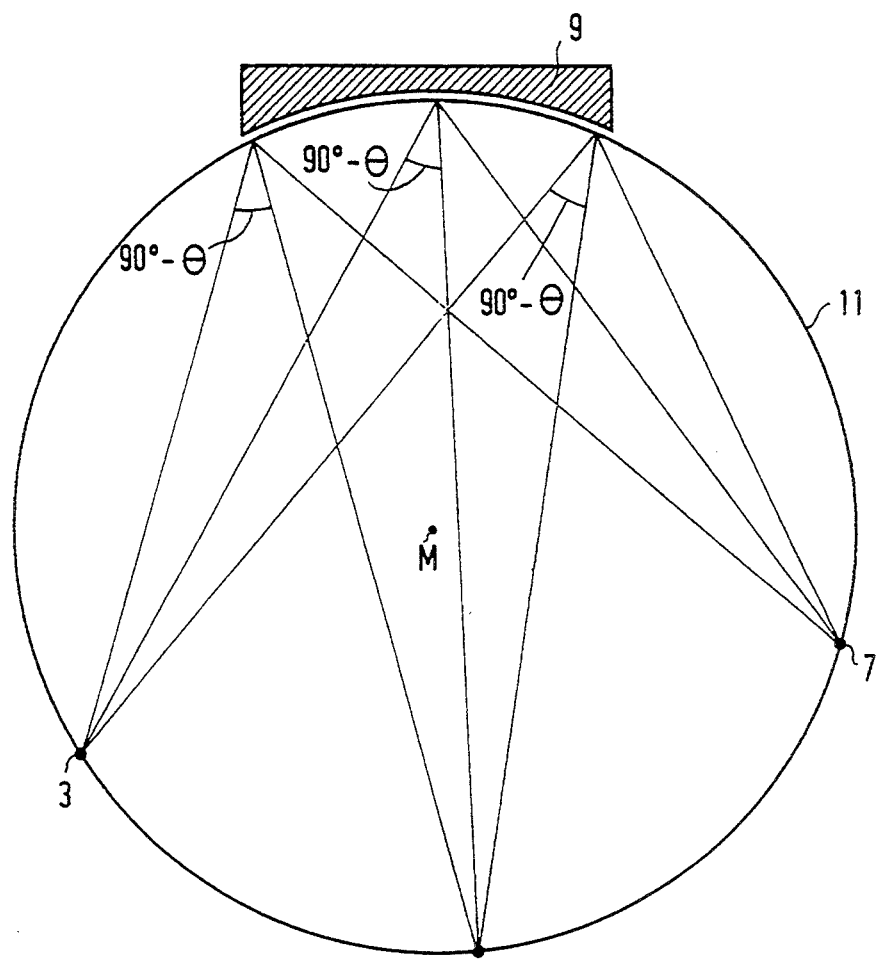
FIG. 2 illustrates the principle of a focusing optical system.

The principle of operation of the scanning unit 1 is based on focusing optics. To this end, the X-ray source 3, the focused image thereof (situated on the X-ray detector 7) and the analysis crystal 9 are situated on the same focusing circle 11. This circle 11 is the so-called Rowland circle. The principle of focusing optics is shown in FIG. 2 in the case of a perfect crystal. Therein, the angle $\theta$ enclosed by the direction of the crystal faces relative to the direction of incidence of the radiation to be analysed, always has the same value. The radius of curvature of the crystal 9 equals twice the radius or diameter (2R) of the Rowland circle 11 having the centre M.

The X-ray source 3 may be, for example a centre 13 of an entrance slit 15 as shown in FIG. 1. An X-ray generator 17 irradiating a specimen 19 to be analysed is then situated behind the entrance slit 15. X-rays emanating from the specimen 19 are subsequently analysed via the entrance slit 15 situated on the Rowland circle 11. The advantage of an arrangement of this kind resides in the fact that a comparatively large part of the surface of the specimen 19 can be irradiated, so that properties are averaged over said part.

Another possibility (not shown) consists in the positioning of the specimen 19 itself on the Rowland circle 11, the specimen then being excited at a point on the surface by means of an electron beam as in the cited United States Patent Specification. Such local excitation generates X-rays to be analysed which are incident in front of the scanning unit as if an entrance slit were present.

Another possibility consists in the localization of the desired region to be analysed by means of a slit on the X-ray detector (not shown).

The scanning unit 1 also comprises a plate 21 via which the X-ray detector 7 and the crystal 9 are mechanically interconnected, said plate also being referred to as a Rowland plate hereinafter.

For the scanning of the spectrum emitted by the specimen 19 to be analysed, the crystal 9 performs a linear motion relative to the X-ray source 3. The X-ray source 3 is chosen to occupy a fixed position, for example in the cast of the scanning unit, because the specimen 19 can then be invariably analysed in the same way at any instant during scanning.

The X-rays emanating from the specimen 19 are incident on the surface 20 of the crystal 9. Due to the displacement of the crystal 9, in response to each displacement the crystal surface 20 assumes a different orientation relative to the fixed pick-up direction, denoted by the arrow 35, for the analysis of the spectrum. The crystal positions shown in FIG. 1 are the two extreme positions wherebetween the crystal 9 can be displaced. One of the positions is denoted by a dashed line, like in the FIGS. 3b and 4. The radiation selected by the crystal 9 is subsequently incident on the X-ray detector 7 which moves, simultaneously with the crystal, along the Rowland circle 11 being tilted about the X-ray source 3. During scanning, the X-ray detector 7 describes a lobe-shaped curve about the X-ray source 3.

The displacement of the crystal 9 is realised by motion of the Rowland plate 21 which is driven by means of a linear motion mechanism. The detector motion, synchronized with the displacement of the crystal 9, is derived from the motion of the Rowland plate 21 and can be realised in various ways which will be described in detail hereinafter.

The X-ray detector 7 is driven from a drive centre C situated on the Rowland plate 21. The linear motion mechanism comprises a first guide 23 and a second guide 25. The first guide 23 is connected to the plate 21 via a first point of attachment 27, referred to as the drive point, the second guide 25 being connected thereto via a second point of attachment 29 which is referred to as the shift point. These points of attachment 27, 29 may be, for example bearing points. The first guide 23 is movable from the drive point 27 in the drive direction 28, the second guide 25 being movable in the shift direction 30. The first guide 23 encloses an angle a relative to the fixed pick-up direction 35. As a result, the displacement of the guide 23 is greater than the corresponding displacement of the crystal 9. This offers the advantage that a nonreproducible adjustment of the guide 23, if any, will have a smaller effect on the precision of the scanning unit 1 than if the drive direction of the guide 23 and the displacement direction of the crystal 9 were to coincide.

The operating principle of the scanning unit 1 will be described with reference to the FIGS. 3a and 3b. The point of intersection of the drive direction 28 and the shift direction 30 determines the position of the X-ray source 3 and, in combination with the pitch between the bearing points 27, 29 (drive point A and shift point Q), the radius R of the Rowland circle 11. In order to realise a fixed pick-up direction 35 (FIG. 1), it is necessary to tilt the Rowland circle 11 about the X-ray source 3. This can be achieved by imposing the following subsidiary conditions on the system (for symmetric crystals):
1. X (=crystal 9), D (=detector 7) and S (=X-ray source 3) are situated on the Rowland circle 11 of diameter 2R,
2. $|SX|=|XD|$,
3. $|SX|=2R\sin\theta$ If the point X is situated on the Rowland circle 11, this point will move along a straight line through S and will rotate according to the condition $|SX|=2R\sin\theta$ imposed from a geometry point of view.

If the drive centre C is chosen to be situated at the centre M of the Rowland circle 11, this point will perform a circular motion about S.

Figure 3A:
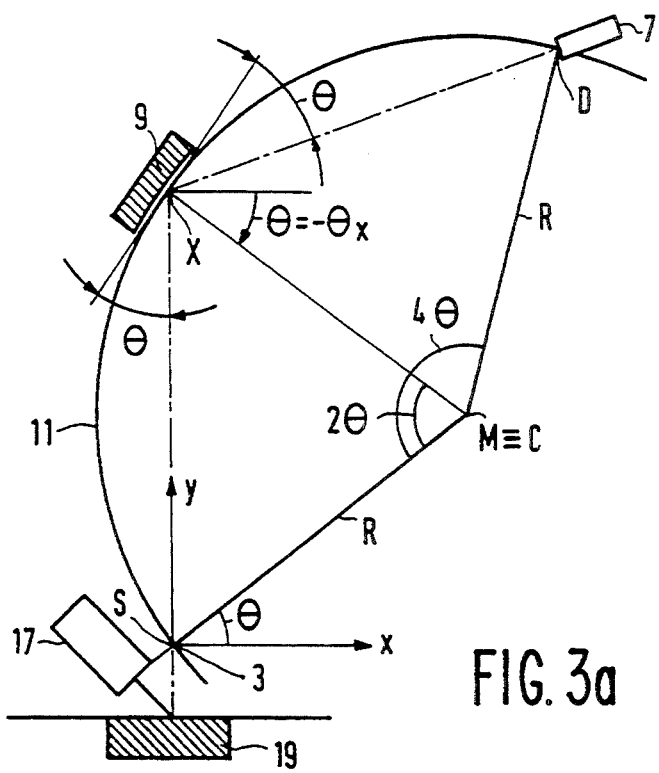
FIG. 3a and 3b shows the goniometric model of the scanning unit in accordance with the invention.
Figure 3B:
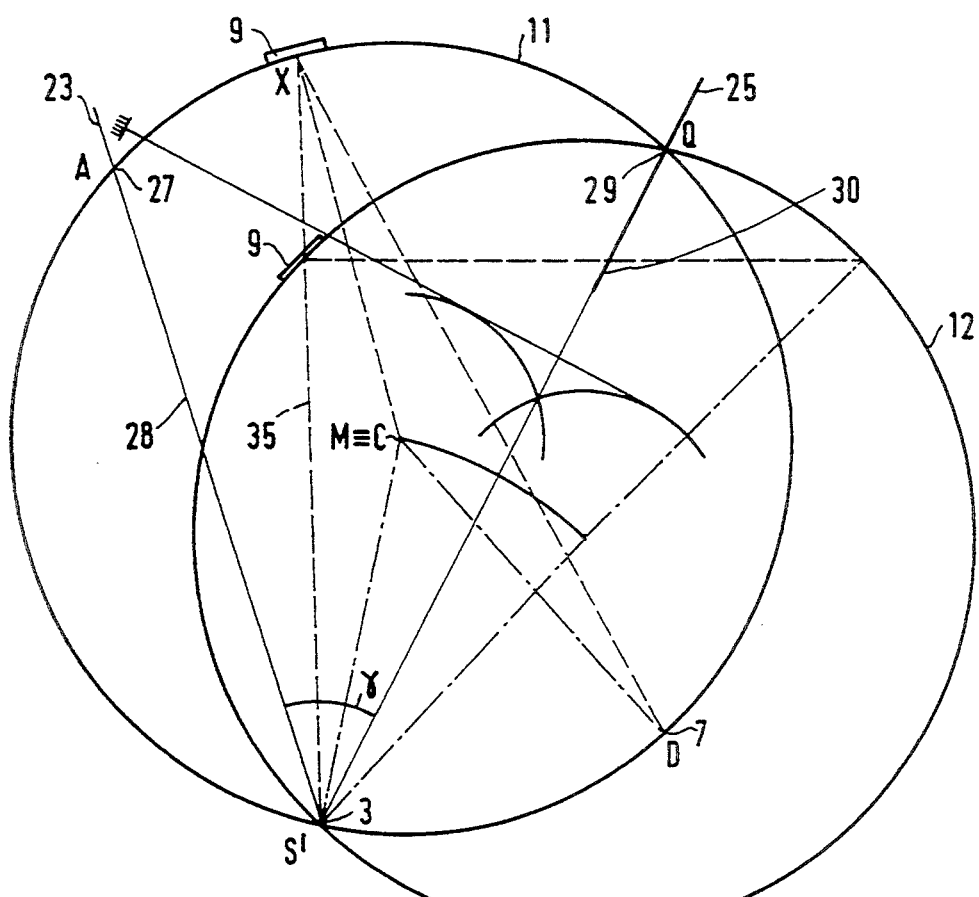

An essential part of the construction is formed by the Rowland plate 21 on which there are situated, as is shown in FIG. 3a, the point of attachment 27 of the first guide 23, also referred to as the drive point A, the point of attachment 29 of the second guide 25, also referred to as the shift point Q, and the crystal 9 (X). The points A, Q and X are situated on the Rowland circle 11 having the centre M and the radius R. A and Q have only one degree of freedom and hence can move only along the guides 23 and 25, respectively. The two directions of motion intersect at S' at an angle γ. The X-ray source 3 is also situated at S'. During scanning, the point A moves along the guide 23, with the result that the point Q is shifted along the guide 25. The position of the second guide 25, notably the shift point Q, is chosen so that its displacement is minimum. Its position is determined by choosing the angle γ. The guide 25 can thus be constructed as an elastic guide. The circle 12, also referred to as the rolling circle, is then tilted about S'. In the reference situation, S' is also situated on the Rowland circle 11 and the Rowland circle 11 and the rolling circle 12 have the same diameter.

The shape of the Rowland plate 21 can be chosen so as to minimize the amount of material outside the points of attachment 27, 29 of the guides 23, 25, the drive centre of the X-ray detector 7 and the crystal 9 while sustaining adequate rigidity, so that a compact scanning unit 1 is obtained. FIG. 1 shows an example thereof.

As has already been stated, more than one configuration is feasible to realise the detector motion.

A first possibility is shown in FIG. 1. In this case the drive centre C coincides with the centre M of the mechnical Rowland circle 11. A segment of circle 33 is pivotably secured at the centre M. Around the segment of circle 33 there is guided a rolling wire 37 which is biased by a separate tension wire 39. The X-ray detector 7 is mechanically coupled to the segment of circle 33 via an arm 31. When the centre M of the Rowland circle 11 pivots about the X-ray source 3 during scanning, the segment of circle 33 will roll along the rolling wire 37, thus imparting a pivoting motion to the X-ray detector 7. When the transmission ratio is suitably chosen, the X-ray detector 7 will perform the desired motion. In the described construction, 1:3 is a suitable transmission ratio; this ratio can be realised by choosing the radius of the segment of circle 33 to be 1/6 of the diameter of the Rowland circle 11. The requirement $|SX|=|XD|$ will also be satisfied if the detector 7 is coupled to the point M via an arm construction having a length R, being the radius of the Rowland circle 11, and if the detector is driven with a transmission ratio 1:3.

Figure 4:
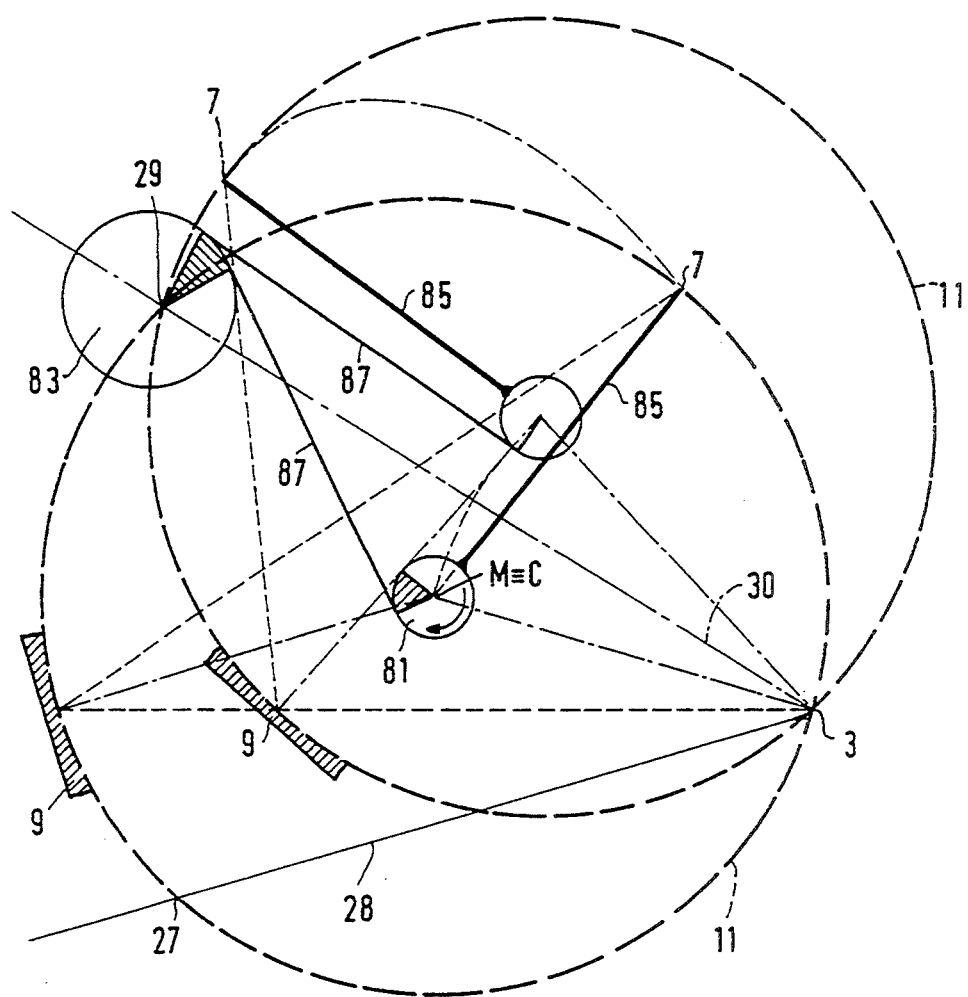
FIG. 4 shows diagrammatically a second embodiment of the scanning unit in accordance with the invention, the detector being driven from the centre of the Rowland circle.

A second possibility, shown in FIG. 4, consists in that a drive wheel 81, 83 is secured at the drive centre C as well as at the shift point 29. The detector 7 is again mechanically connected to the drive wheel 81 via an arm construction 85. A drive belt 87 is guided on the drive wheels 81, 83. For example, when the drive wheel 81 is driven at the drive centre C and has a diameter amounting to half the diameter of the drive wheel 83 at the shift point 29, the detector will be driven with a transmission ratio of approximately 1:2.

Figure 5:
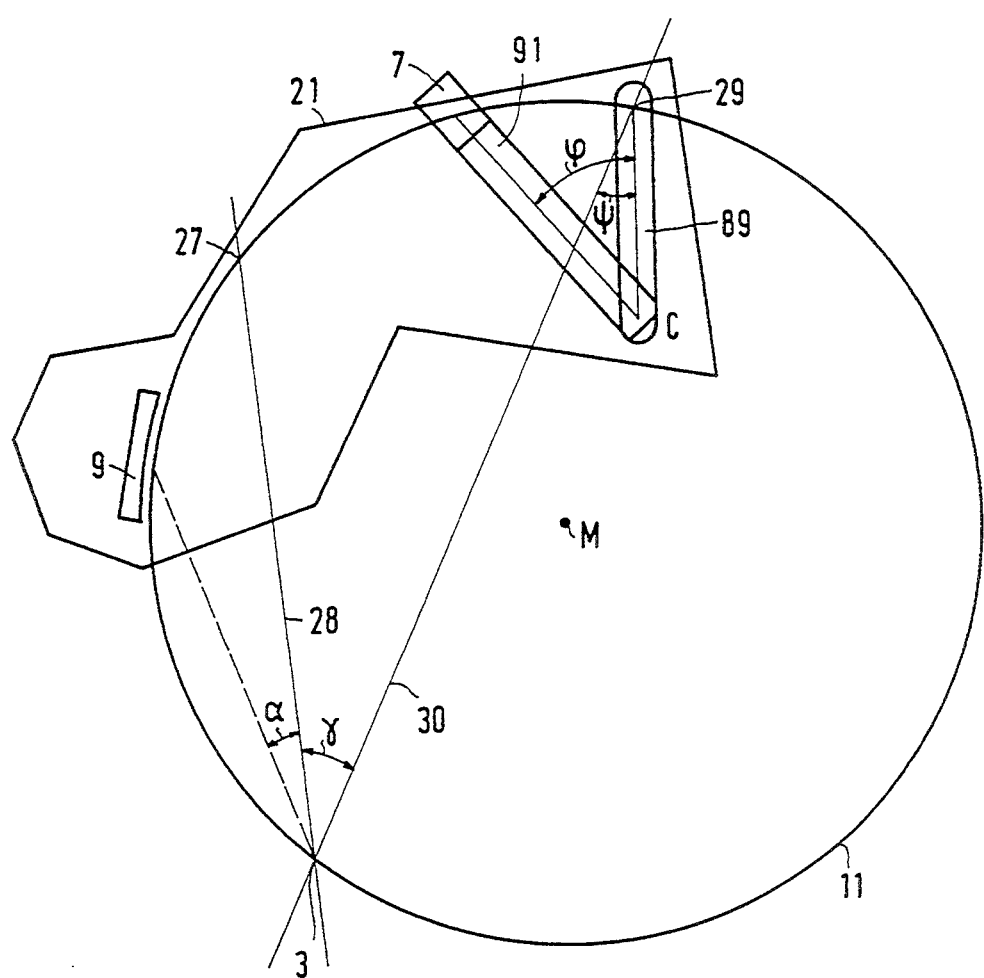
FIG. 5 shows diagrammatically an embodiment of the scanning unit in accordance with the invention in which the detector is driven from a point on the Rowland plate which is not coincident with the centre of the Rowland circle.

However, it is not necessary to make the drive centre C coincide with the centre M of the Rowland circle. For the detection of heavier elements, that is to say with smaller angles, the distance between the X-ray source and the analysis crystal is comparatively small. The distance between the X-ray source and the analysis crystal, however, should have at least a minimum value so as to enable reproducible measurements. Because this distance is given by $2R \sin\theta$, where R is the radius of the Rowland circle, the distance can be adapted by enlarging the Rowland circle. This may lead to a comparatively voluminous construction. When the drive centre is not made to coincide with the centre of the large Rowland circle, the dimensions can still remain acceptable. This embodiment is shown in FIG. 5. On the Rowland plate 21 there is secured an arm 89 whose length is given substantially by:

$$\frac{1}{2} 2R/\cos\Delta$$

where 2R is the diameter of the Rowland circle 11 and $\Delta$ is the deviation of $\theta$ from the angle between the shift direction 30 and the direction of motion 35 of the crystal 9. $\gamma$ is the angle enclosed by the drive direction 28 and the shift direction 30. This arm 89 is arranged at a fixed angle $\psi$ relative to the shift direction, one of its ends being secured at the shift point 29, its other end being secured at the drive centre C whose position is defined by the length of the arm 89 and the choice of the angle $\psi$. The detector 7 is mechanically coupled to said arm 89 at an angle $\psi$, via an arm 91 at the drive centre C. The length of the arm 91 and the value of the angle $\psi$ are chosen so that the image focused on the detector 7 is situated on the Rowland circle 11. When the first guide 23 is driven from the drive point 27, the second guide 25 will be shifted from the shift point 29 in the shift direction 30, so that the motion is transmitted to the arm construction 89, 91 and hence to the detector 7.

Figure 6:
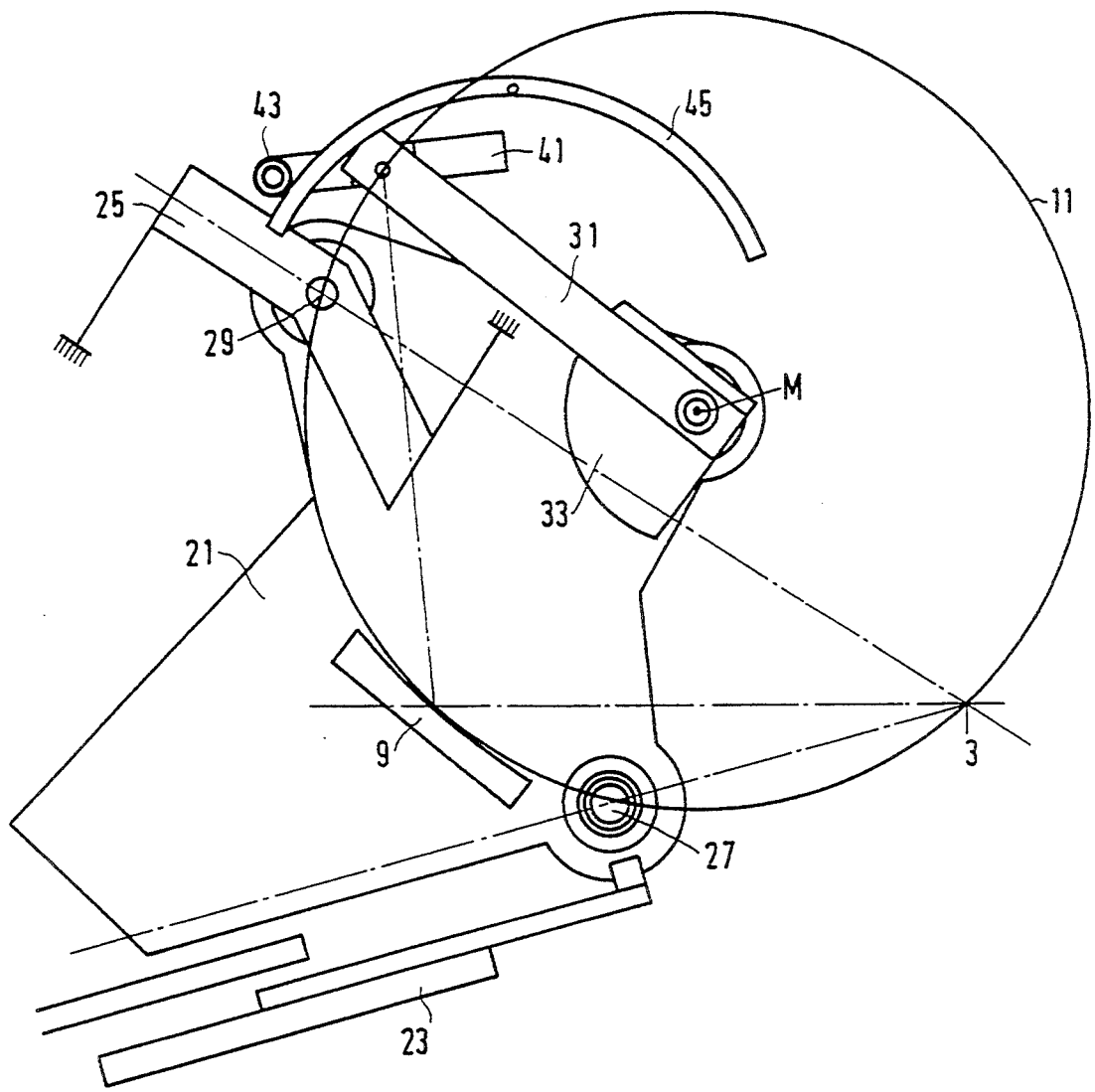
FIG. 6 shows diagrammatically a first embodiment of the scanning unit in accordance with the invention which includes correction of viewing direction.

Correction of the direction of viewing is required to align the X-ray detector 7 with respect to the crystal 9 during the displacement. A first possibility in this respect is shown in FIG. 6. Therein, the detector motion is driven from the centre M of the Rowland circle 11 by means of a segment of circle 33 of the kind already described with reference to FIG. 1. The X-ray detector 7 is mounted on a detector mounting bracket 41 on which a runner 43 is secured, said runner running on a track 45 provided adjacent the X-ray detector 7. The track 45 also suppresses detector motions perpendicularly to the plane of motion, resulting in a substantial improvement of the rigidity of the system in the direction perpendicular to the plane of motion.

Figure 7:
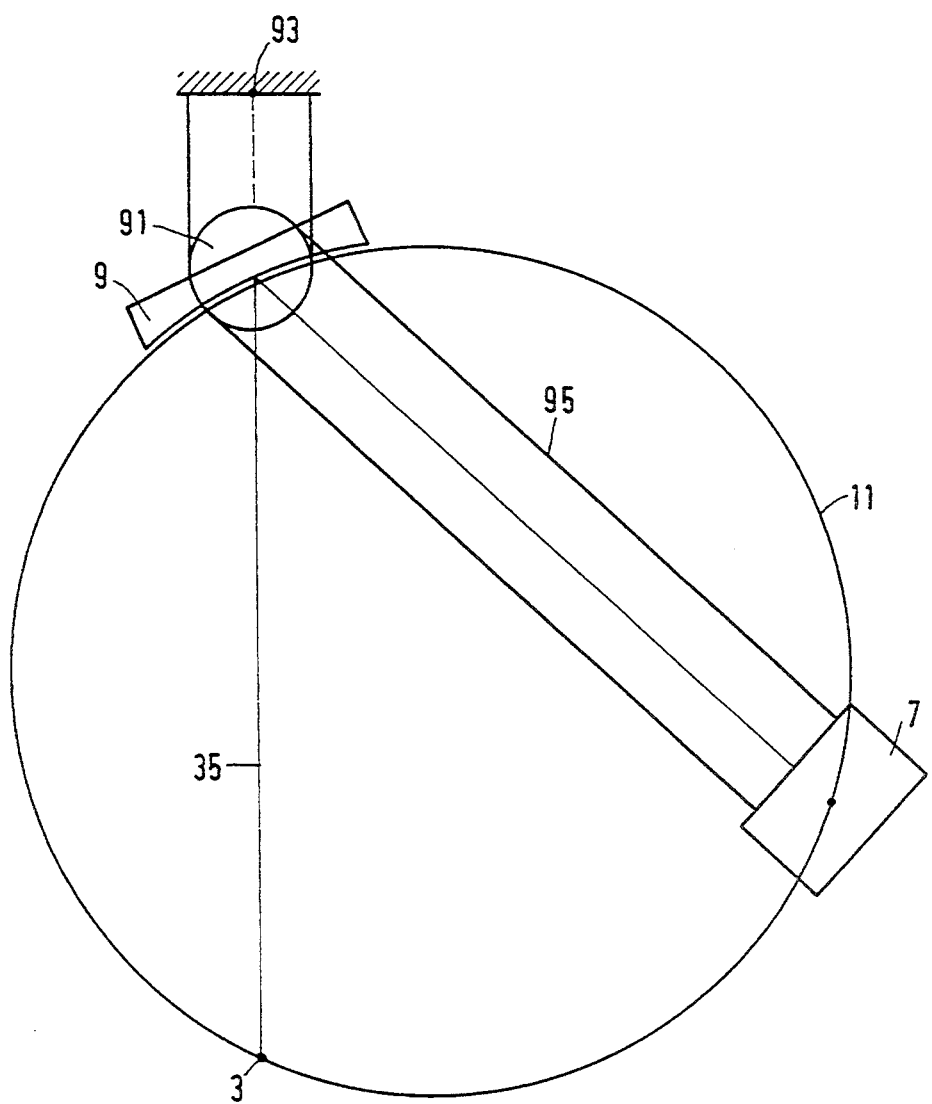
FIG. 7 shows diagrammatically a second embodiment of the scanning unit in accordance with the invention which includes correction of viewing direction.

A second possibility for correction of the viewing direction is shown in FIG. 7 and consists in that the crystal holder or the analysis crystal 9 is provided with a guide roller 91, a wire 95 guided on the guide roller 91 being tensioned between the X-ray detector 7 and a fixed point 93 outside the Rowland circle 11, in the virtual prolongation of the fixed pick-up direction 35. The direction of the force exerted on the detector 7 is then such that the detector is always oriented towards the crystal 9.

Both possibilities for correction of the viewing direction can be used for the three described embodiments for implementing the detector motion.

Not only the Rowland plate 21, but also the crystal holder 9 is an important component of the construction, because the reproducibility of the scanning unit 1 depends to a substantial degree on the crystal holder. The crystal holder 9 is constructed as a crystal turret 9 so that a crystal can be exchanged comparatively quickly.

Figure 8:
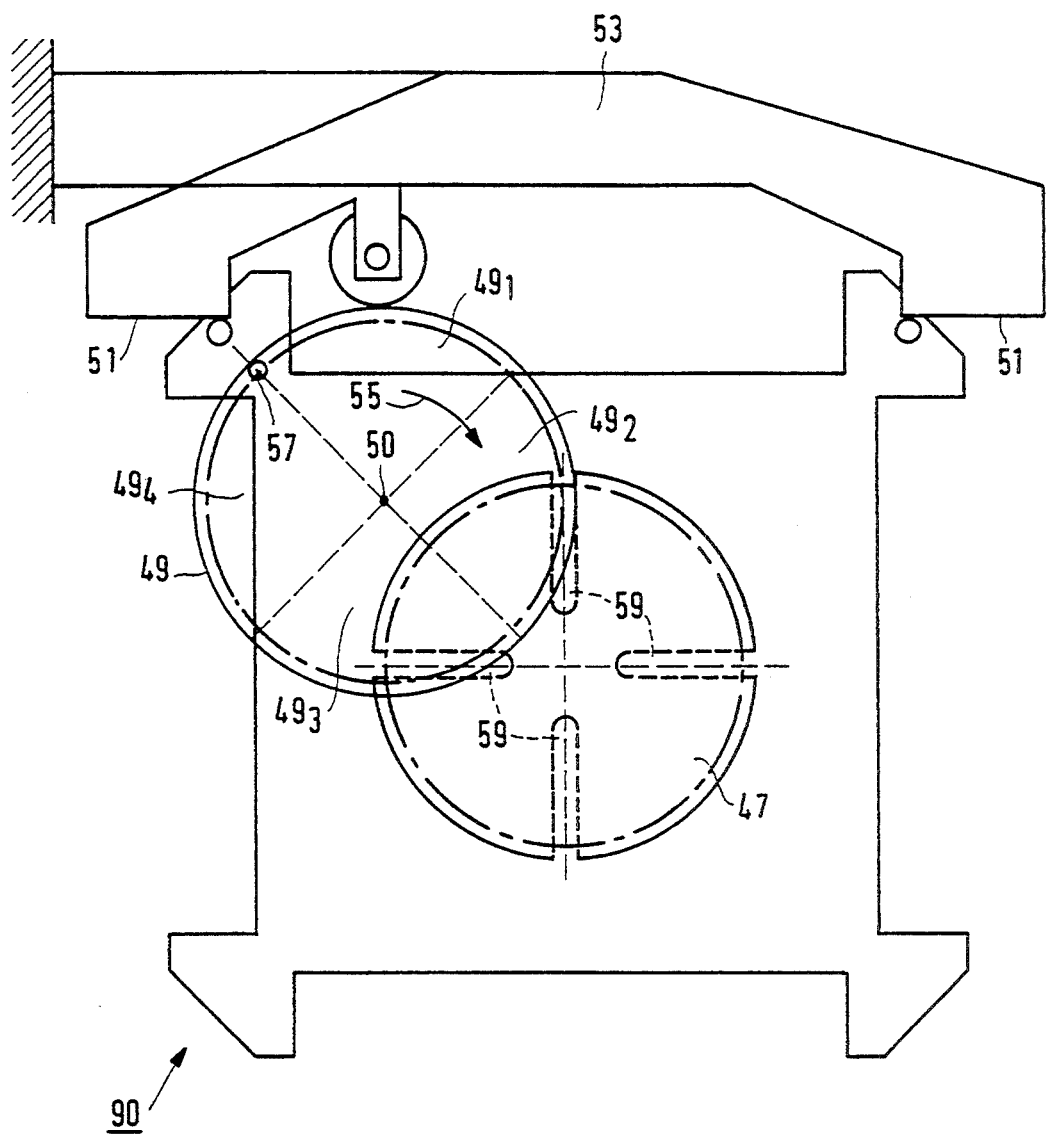
FIG. 8 shows an embodiment of the crystal turret suitable for use in a scanning unit in accordance with the invention.

FIG. 8 shows an embodiment of a four-crystal turret 90 with a maltese cross 47 in the stationary state. The crystal turret 90 also comprises a cam disc 49 whereby the maltese cross 47 is rotated and with which a stop 51 can cooporate so as to enable rotation or not. The stop 51 is suspended in a leaf spring guide 53. When the cam disc 49 is rotated about a shaft 50 in a direction as denoted by an arrow 55, successively the stop 51 is raised, the crystal turret 90 is rotated and the stop 51 is lowered again. To this end, in the present embodiment the cam disc 49 is subdivided into four 90° segments $49_1$, $49_2$, $49_3$, and $49_4$. The latter segment is intended for the running out and starting of the drive motor. The crystal turret 90 is advanced to the next position by cooperation between a projection 57, provided on the cam disc 49, and one of the recesses 59 of the maltese cross 47. Once the turret reaches the next position, the stop 51 is lowered and the crystal turret is blocked, rotation thus being stopped. When the crystal turret 90 is drivable in two directions, the exchanging of the crystal can be faster, so that adjustment to the desired wavelength is also faster.

The guide 23 shown in FIG. 1 can be driven by means of a step motor or by means of a servo positioning system. The choice between these two systems is determined by the requirements imposed on the guide. A step motor drive implies the choice of a high-quality guide in view of the requirements imposed as regards reproducibility and linearity. A servo drive imposes less severe requirements on the guide, because it is used in combination with a measuring ruler.

Diffraction crystals generally exhibit a given degree of asymmetry, i.e. the lattice faces do not extend perfectly parallel to the crystal surface. Therefore, crystal position control is required so as to keep the spread of the focus on the X-ray detector 7 small. Furthermore, correction is also possible for deviations from the assumed position of the entrance slit relative to the Rowland circle, for positioning tolerances of the crystal and the X-ray source, and for small mechanical tolerances.

In order to minimize the background, the detection slit (not shown) of the X-ray detector 7 may form part of a beam limiter in the vicinity of the detection aperture.

The described construction of the scanning unit 1 allows for the use of crystals of already existing systems. The limited length in combination with the use for large angles enables the use of Johann-type crystals, without degrading the resolution. The manufacture of such a type of crystal is comparatively inexpensive and simple.

An X-ray analysis apparatus comprising a scanning unit of the kind set forth has several applications. On the one hand, such an X-ray analysis apparatus may be constructed as a simultaneous spectrometer. A conventional simultaneous spectrometer comprises a number of channels. Each of these channels is adjusted to a given wavelength. The wavelength for which a channel is reserved are simultaneously and hence comparatively quickly measured, but the number of wavelengths that can be measured is limited by the number of channels available. If one or more of the fixed channels is replaced by a scanning unit in accordance with the invention, the speed of a simultaneous spectrometer is retained and at the same time the flexibility of the apparatus is substantially increased. The use of more than one scanning unit increases the number of elements that can be measured by means of the same apparatus. The number of scanning units in combination with the $\theta$ range thereof can even be chosen so that the complete range of elements can be scanned. In this manner the speed of a simultaneous spectrometer can again be retained and a sequential spectrometer of higher sensitivity can be realised. The higher sensitivity on the one hand and the possibility of simultaneous measurement on the other hand will substantially reduce also the measurement time per specimen, thus benefiting the specimen throughput.

On the other hand, the X-ray analysis apparatus in accordance with the invention can be constructed as a sequential spectrometer. In order to enable scanning of the customary range of elements (from borium to uranium), corresponding to a $\theta$ range of from 6° to 72°, adequate space should be present in the diffraction plane so as to allow tilting of the Rowland circle through an angle of 66°. Because the radius of the Rowland circle is determined by the source-crystal distance required for suitable resolution, it is desirable to subdivide the complete scanning range into a number of scanning sub-ranges. Each scanning sub-range can then be scanned by its own scanning unit having a Rowland diameter adapted to the relevant sub-range. The possibility of selective use of a scanning unit for a limited element range will result in a substantial improvement of the price-performance ratio of the X-ray analysis apparatus. Moreover, the contemporary X-ray detectors are only suitable for sub-ranges of the customary range of elements.

We claim:

1. An X-ray analysis apparatus, comprising a scanning unit with an X-ray source, a crystal holder, an X-ray detection system with an X-ray detector and a motion mechanism for effecting a coupled displacement of the crystal holder and the X-ray detector relative to the X-ray source, a point of the X-ray source, a point of the crystal holder and a point of the X-ray detector remaining on a circle having a constant diameter, referred to herein as a Rowland circle, during said coupled displacement, which coupled displacement effects a rectilinear displacement of the point of the crystal holder relative to the point of the X-ray source along a fixed line directed between the point of the crystal holder and the point of the X-ray source, referred to as the radiation pick-up direction, wherein the motion mechanism of the scanning unit comprises a base plate, referred to herein as a Rowland plate, to which the crystal holder is fixed, first guide guiding a first point of the Rowland plate, which first guide is arranged such that the first point can be displaced along a line, referred to herein as a drive direction from a drive point, a second guide guiding a second point of the Rowland plate, which second guide is arranged such that the second point can be displaced along a line, referred to herein as a shift direction from a shift point, the drive direction enclosing an acute angle $\alpha$ relative to said fixed pick-up direction and an acute angle $\gamma$ relative to said shift direction, said coupled displacement of the crystal and the X-ray detector relative to the X-ray source varying an angle $\theta$ enclosed between said fixed pick-up direction and a tangent to the Rowland circle at said point on the crystal over a scanning range within or equal to a range between fixed extreme values of the angle $\theta$, and said angle $\gamma$ being chosen to minimize the displacement of said second point along the shift direction during a coupled displacement of the crystal holder and the X-ray detector relative to the X-ray source effecting variation of the angle $\theta$ from one of the fixed extreme values to the other.

2. An X-ray analysis apparatus as claimed in claim 1, characterized in that the second guide is constructed as an elastic guide.

3. An X-ray analysis apparatus as claimed in claim 1, characterized in that the mechanism is attached to the Rowland plate at a third point.

4. An X-ray analysis apparatus as claimed in claim 3, characterized in that adjacent the first, second and third points the amount of material of the Rowland plate is minimized while sustaining adequate rigidity.

5. An X-ray analysis apparatus as claimed in claim 3, characterized in that the third point is coincident with the center of the Rowland circle.

6. An X-ray analysis apparatus as claimed in claim 5, characterized in that at the third point a member having a periphery shaped as a segment of circle is pivotably secured, the detector being mechanically coupled to said member and a wire, being guided on said periphery such that said member can roll along said wire in order to impart to the detector a pivot motion linked to the motion of the crystal holder.

7. An X-ray analysis apparatus as claimed in claim 6, characterized in that the radius of the segment of circle amounts to 1/6 of the diameter of the Rowland circle.

8. An X-ray analysis apparatus as claimed in claim 3, characterized in that at the third point there is provided a first drive wheel whereto the detector is mechanically coupled, at the shift point there being provided a second drive wheel, a drive belt being guided on said drive wheels, a ratio of diameters of the first and second drive wheels being defined by a transmission ratio.

9. An X-ray analysis apparatus as claimed in claim 3, characterized in that on the Rowland plate there is secured an arm having a length substantially equal to $$\tfrac{1}{2} 2R/\cos\Delta$$

said arm being attached to the shift point of the second guide and to the third point and having a position determined by the length of the arm and a direction which encloses a fixed angle $\psi$ relative to the shift direction, the X-ray detector being mechanically coupled to said arm, 2R being the diameter of the Rowland circle and $\Delta$ being a deviation of $\theta$ relative to an angle $\gamma + \alpha$ enclosed by the shift direction and the fixed pick-up direction.

10. An X-ray analysis apparatus as claimed in claim 6, characterized in that for directional adjustment the detector is mounted on a mounting bracket on which there is provided a runner which can run on a track provided adjacent the detector.

11. An X-ray analysis apparatus as claimed in claim 6, characterized in that for directional adjustment of the detector a guide roller is secured to the crystal holder, a wire which is tensioned between on the one side the X-ray detector and on the other side a fixed point situated outside the Rowland circle and in a virtual prolongation of the fixed pick-up direction being guided on said guide roller.

12. An X-ray analysis apparatus as claimed in claim 1, characterized in that the first guide is driven by means of a step motor.

13. An X-ray analysis apparatus as claimed in claim 1, characterized in that the first guide is driven by means of a servo positioning system.

14. An X-ray analysis apparatus as claimed in claim 1, characterized in that the crystal holder is constructed as a crystal turret.

15. An X-ray analysis apparatus as claimed in claim 14, characterized in that the crystal turret can be driven in two directions.

16. An X-ray analysis apparatus as claimed in claim 1, characterized in that the crystal holder comprises a control device for the crystal position.

17. An X-ray analysis apparatus as claimed in claim 1, characterized in that the detector of the scanning unit comprises a detection slit which forms part of a beam limiter.

18. An X-ray analysis apparatus as claimed in claim 1, configured as a simultaneous spectrometer comprising a number of fixed channels, characterized in that at least one of the fixes channels comprises said scanning unit.

19. An X-ray analysis apparatus as claimed in claim 1, configured as a sequential spectrometer, characterized in that the scanning range thereof can be adjusted to be less than the entire range between the fixed extreme values of the angle $\theta$.

20. A scanning unit suitable for use in an X-ray analysis apparatus, said scanning unit comprising an X-ray source, an X-ray source, a crystal holder, an X-ray detection system with an X-ray detector and a motion mechanism for effecting a coupled displacement of the crystal holder and the X-ray detector relative to the X-ray source, a point of the X-ray source, a point of the crystal holder and a point of the X-ray detector remaining on a circle having a constant diameter, referred to herein as a Rowland circle, during said coupled displacement, which coupled displacement effects a rectilinear displacement of the point of the crystal holder relative to the point of the X-ray source along a fixed line directed between the point of the crystal holder and the point of the X-ray source, referred to as the radiation pick-up direction, wherein the motion mechanism of the scanning unit comprises a base plate, referred to herein as a Rowland plate, to which the crystal holder is fixed, a first guide guiding a first point of the Rowland plate, which first guide is arranged such that the first point can be displaced along a line, referred to herein as a drive direction from a drive point, a second guide guiding a second point of the Rowland plate, which second guide is arranged such that the second point can be displaced along a line, referred to herein as a shift direction from a shift point, the drive direction enclosing an acute angle $\alpha$ relative to said fixed pick-up direction and an acute angle $\gamma$ relative to said shift direction, said coupled displacement of the crystal and the X-ray detector relative to the X-ray source varying an angle $\theta$ enclosed between said fixed pick-up direction and a tangent to the Rowland circle at said point on the crystal over a scanning range within or equal to a range between fixed extreme values of the angle $\theta$, and said angle $\gamma$ being chosen to minimize the displacement of said second point along the shift direction during a coupled displacement of the crystal holder and the X-ray detector relative to the X-ray source effecting variation of the angle $\theta$ from one of the fixed extreme values to the other.

* * * * *